United States Patent [19]

Hem et al.

[11] 4,059,681

[45] * Nov. 22, 1977

[54] STABLE DRIED ALUMINUM HYDROXIDE GEL

[75] Inventors: Stanley L. Hem, West Lafayette; Joe L. White, Lafayette, both of Ind.

[73] Assignee: Purdue Research Foundation, Lafayette, Ind.

[*] Notice: The portion of the term of this patent subsequent to Oct. 7, 1992, has been disclaimed.

[21] Appl. No.: 566,254

[22] Filed: Apr. 9, 1975

Related U.S. Application Data

[63] Continuation-in-part of Ser. No. 360,043, May 14, 1973, abandoned.

[51] Int. Cl.$^2$ .................. C01B 31/24; A01N 11/00; A61K 33/10; C01F 7/02
[52] U.S. Cl. .................. 423/419 P; 423/427; 423/630; 424/156; 424/157
[58] Field of Search ............... 423/419, 420, 421, 422, 423/428, 430, 625, 628, 629; 424/154, 156, 157, 158

[56] References Cited

U.S. PATENT DOCUMENTS

| | | | |
|---|---|---|---|
| 2,783,179 | 2/1957 | Crote et al. | 423/419 |
| 2,958,626 | 11/1960 | Schenck | 423/430 |
| 3,115,387 | 12/1963 | Lewin | 423/422 |
| 3,272,704 | 9/1966 | Beekman | 424/156 |
| 3,773,918 | 11/1973 | Beekman | 423/629 |
| 3,857,938 | 12/1974 | Rovati et al. | 424/157 |
| 3,911,090 | 10/1975 | Hem et al. | 423/427 |

OTHER PUBLICATIONS

The Pharmacopoeia of The United States of America, 13th Revision, 1947 Mack Publishing Co., Easton, Pa., p. 27.

Primary Examiner—O. R. Vertiz
Assistant Examiner—Gary P. Straub
Attorney, Agent, or Firm—John R. Nesbitt

[57] ABSTRACT

Stable dried aluminum hydroxide gels possessing the high acid reactivity of liquid aluminum hydroxide gel are prepared by drying the gel from non-aqueous solvents.

4 Claims, 7 Drawing Figures

FIG. I EFFECT OF AGING AT 40° ON THE ROSSETT RICE TIME OF ALUMINUM HYDROXIDE GELS FRIED FROM: WATER (□); ETHANOL, USP (●); 75% ETHANOL, USP: 25% BENZENE(•); AND 50% ETHANOL, USP: 50% BENZENE(○)

FIG. 1 EFFECT OF AGING AT 40° ON THE ROSSETT RICE TIME OF ALUMINUM HYDROXIDE GELS FRIED FROM: WATER (□); ETHANOL, USP (○); 75% ETHANOL, USP: 25% BENZENE(•); AND 50% ETHANOL, USP: 50% BENZENE (⊚)

DTA THERMOGRAM OF DRIED ALUMINUM HYDROXIDE GEL DRIED FROM WATER.

DTA THERMOGRAM OF DRIED ALUMINUM HYDROXIDE GEL DRIED FROM ETHANOL, USP.

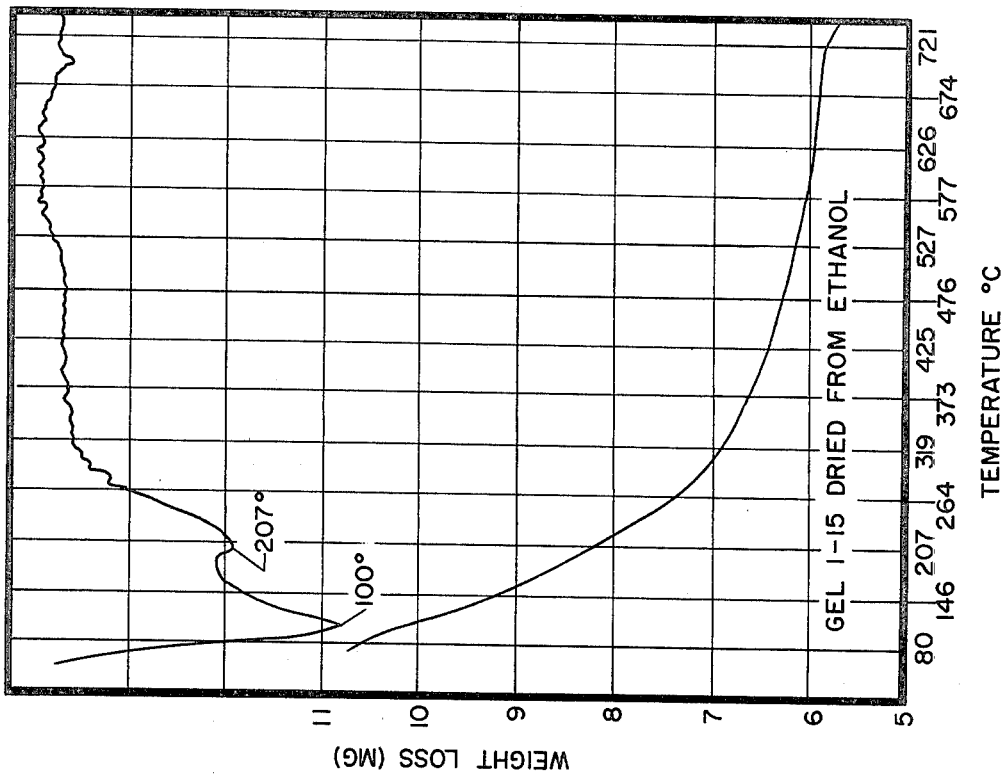
FIG. 5 TGA ANALYSIS OF DRIED ALUMINUM HYDROXIDE GEL DRIED FROM ETHANOL, U.S.P. (LOWER CURVE) DTG ANALYSIS (UPPER CURVE)
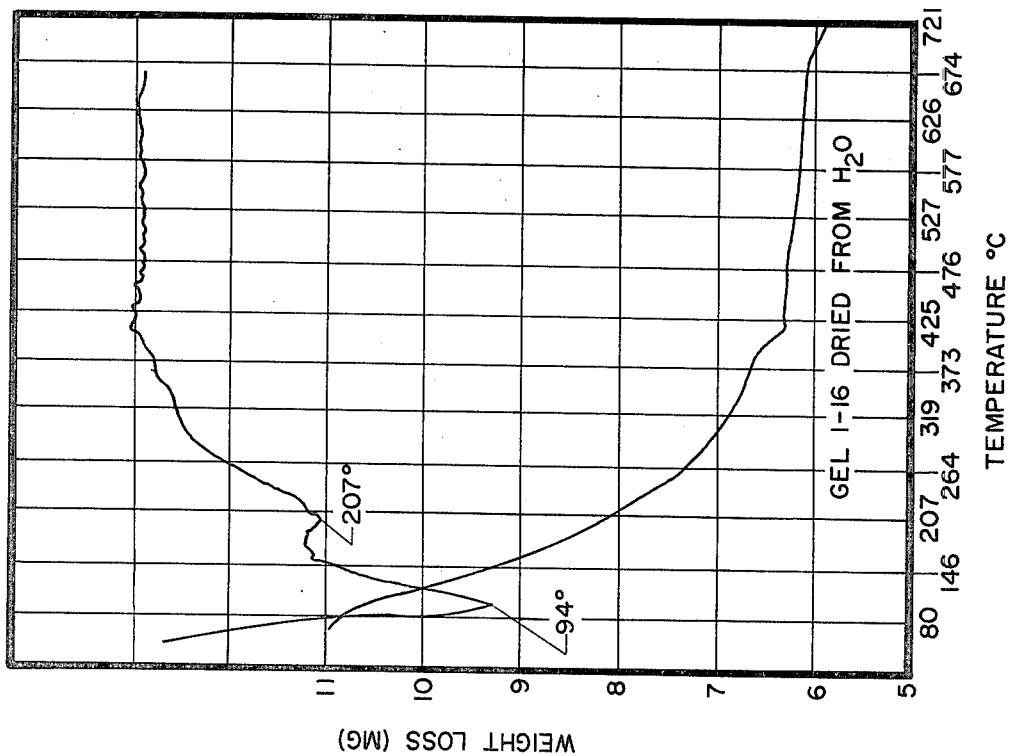
FIG. 4 TGA ANALYSIS OF DRIED ALUMINUM HYDROXIDE GEL DRIED FROM WATER (LOWER CURVE) DTG ANALYSIS (UPPER CURVE)

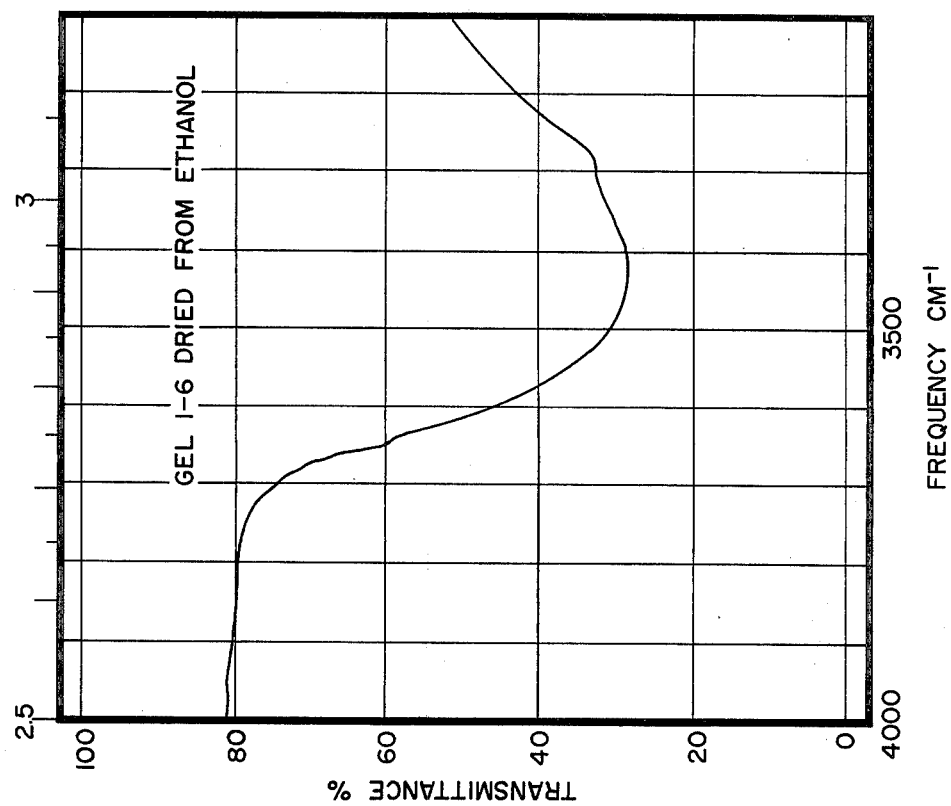
FIG. 7 IR SPECTRUM OF DRIED ALUMINUM HYDROXIDE GEL DRIED FROM ETHANOL U.S.P.
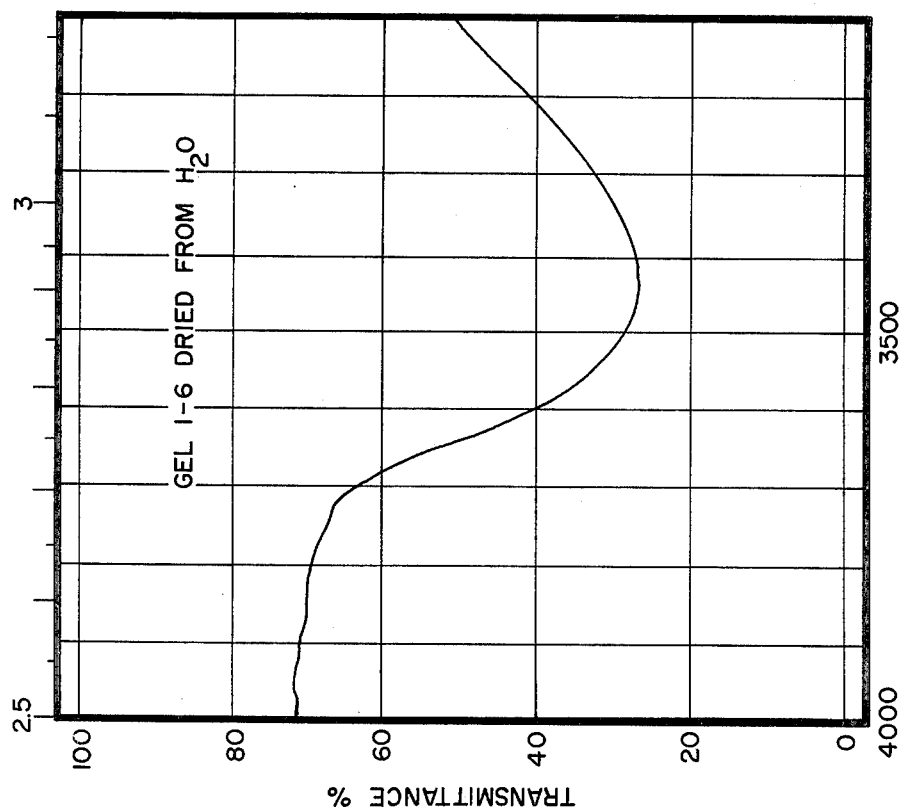
FIG. 6 IR SPECTRUM OF DRIED ALUMINUM HYDROXIDE GEL DRIED FROM WATER

4,059,681

STABLE DRIED ALUMINUM HYDROXIDE GEL

RELATED APPLICATION

This application is a continuation-in-part of U.S. Patent application, Ser. No. 360,043, filed May 14, 1973, and entitled "Stable Dry Aluminum Hydroxide Gel", now abandoned.

FIELD OF THE INVENTION

This invention relates to dried aluminum hydroxide gels which possess the same level of acid reactivity as liquid aluminum hydroxide gel and retain this level of reactivity on aging.

This invention further relates to a process for stabilizing dried aluminum hydroxide gel so that it retains its initial level of acid reactivity on storage.

BACKGROUND OF THE INVENTION

At the present time, aluminum hydroxide gel is the most widely used antacid as it possesses many of the properties of the ideal antacid. It neutralizes a large quantity of acid, maintains the pH in the stomach between 3 to 5 while reacting, and does not cause alkalosis. When aluminum hydroxide gel is dried to produce a powder which can be used to prepare solid dosage forms, however, its total reactivity, as well as its rate of reaction with acid, is decreased. In addition, increasingly greater losses in reactivity occur when the dried aluminum hydroxide is aged at ambient or elevated temperatures. As a result of this instability, liquid aluminum hydroxide gels are considerably more effective than dried aluminum hydroxide gels. However, those individuals requiring antacid therapy would prefer a portable solid dosage form which is more convenient to use than the liquid gel. Attempts have been made to improve the stability and reactivity of dried aluminum hydroxide gel by adding glycine or carboxylic acids to the liquid gel prior to drying. Another approach has been to combine aluminum hydroxide with magnesium hydroxide gels prior to drying. None of these approaches has been completely successful in producing a dried aluminum hydroxide gel which possesses and retains the acid reactivity of liquid aluminum hydroxide gel.

SUMMARY OF THE INVENTION

It has now been found that stable, highly reactive dried aluminum hydroxide gels are obtained when the aqueous solvent present after the liquid aluminum hydroxide gels has been prepared is replaced with a water miscible non-aqueous solvent, after which the gel is dried by conventional means. The water miscible non-aqueous solvent which can be used in this invention can be any water miscible non-aqueous solvent and includes the lower alkanols having 1 to 5 carbon atoms, e.g., methanol, ethanol, isopropanol and the like, the lower alkanols containing no more than 50% aromatic hydrocarbon such as benzene, toluene and the like, ketones having 2 to 4 carbon atoms, e.g., acetone, methyl ethyl ketone and the like, ethers such as dioxane, diethyl ether, and the like and esters such as ethyl acetate. The preferred solvents are the lower alkanols, in particular, methanol and ethanol; ethanol/benzene mixtures containing 50% or less benzene and acetone.

The dried aluminum hydroxide gel prepared by this invention exhibits the usual physical properties of dried aluminum hydroxide gel and in addition retains the acid consuming capacity and reactivity as measured by the Rossett Rice time of the original gel. The acid consuming capacity is the number of milliliters of 0.1 N hydrochloric acid required to neutralize 1 gram equivalent of $Al_2O_3$ in the final product. The Rossett Rice time is the length of time a quantity of the dry gel equivalent to 300 mgs. of aluminum oxide dispersed in 70 milliliters of 0.1 N hydrochloric acid and 30 milliliters of water at 37° C remains at a pH between 3 to 5 as 0.1 N-hydrochloric acid is added to the mixture at a rate of 4 milliliters per minute.

BRIEF DESCRIPTION OF THE DRAWINGS

These and other aspects of this invention will become evident from the attached drawings and the description below. With reference to the drawing:

FIG. 4 is a Thermal Gravimetric Analysis (TGA) and Differential Thermal Gravimetric Analysis (DTGA) thermogram for aluminum hydroxide gel dried from water.

FIG. 5 is a Thermal Gravimetric Analysis and Differential Thermal Gravimetric Analysis thermogram for aluminum hydroxide gel dried from ethanol.

FIG. 6 is an infra-red spectrograph for aluminum hydroxide gel dried from water.

FIG. 7 is an infra-red spectrograph for aluminum hydroxide gel dried from ethanol.

DESCRIPTION OF THE INVENTION

Dry amorphous aluminum hydroxide gels decrease in acid reactivity when stored at either 25° or 40° C, and normally have no Rossett-Rice reactivity after aging for 6 months at 40° C. Most commercial dried aluminum hydroxide gel lose all of their Rossett-Rice activity after 1 year at 25° C. In contrast, the aluminum hydroxy gels prepared by this invention retain a significant part of their acid reactivity after storage at room temperature and elevated temperature for lengthy periods of time.

Figure 1:
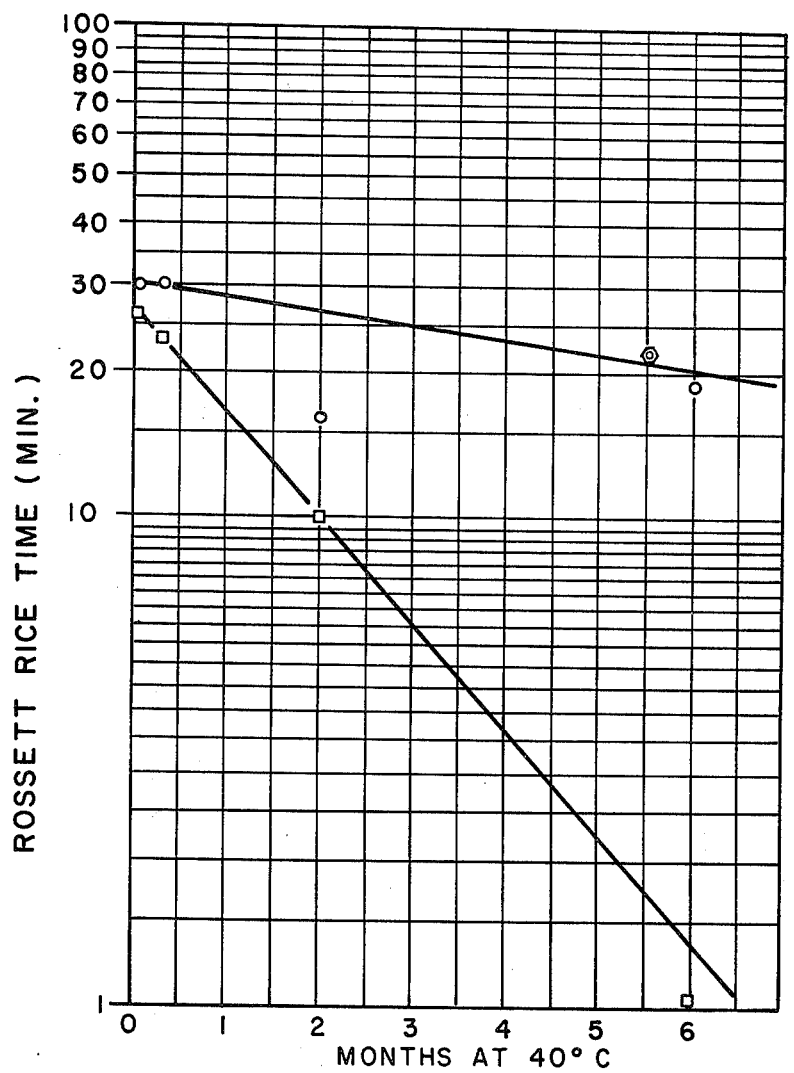
FIG. 1 is a graph showing the effect of aging at 40° C on the Rossett Rice time for aluminum hydroxide gels dried from various media.

The rate of loss of Rossett Rice activity for aluminum hydroxy gels is illustrated in FIG. 1 where the Rossett Rice time for gels dried from water is compared to the date for gels dried from 1) ethanol (USP); 2) 75% ethanol (USP)/25% benzene; and 3) 50% ethanol (USP)/50% benzene. The rate constant for loss of reactivity for gels dried from water is about 0.48 mo$^{-1}$ at 40° C in contrast to about 0.071 mo$^{-1}$ at 40° C for gels dried from the non-aqueous solvents. Thus one-half of the control gel's Rossett Rice reactivity is lost in 1.5 months at 40°. The gels dried from ethanol require 10 months at 40° before one-half of their Rossett Rice reactivity is lost. This is a significant difference which is reflected in a much greater retention of acid reactivity at room temperature by the gels dried from ethanol. The reactivity rate constant of the gels of this invention is less than 0.2 mo$^{-1}$ at 40° C, preferably less than 0.1 mo$^{-1}$ at 40° C and the Rossett Rice Time is greater than 15 minutes, preferably 20 minutes.

Figure 2:
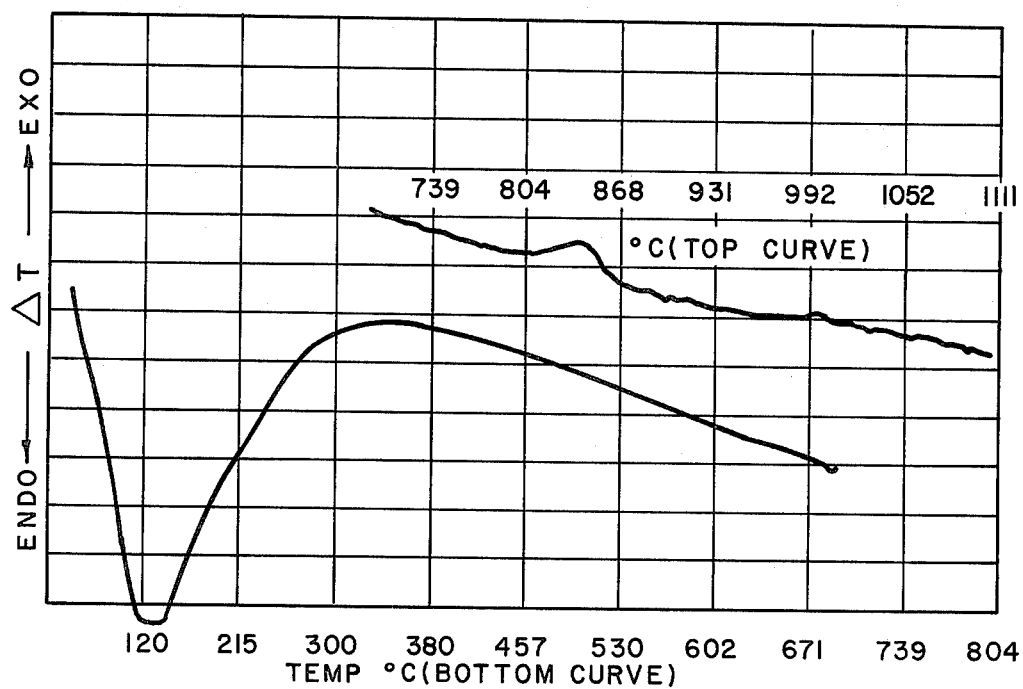
FIG. 2 is a Differential Thermal Analysis (DTA) thermogram for aluminum hydroxide gel dried from water.
Figure 3:
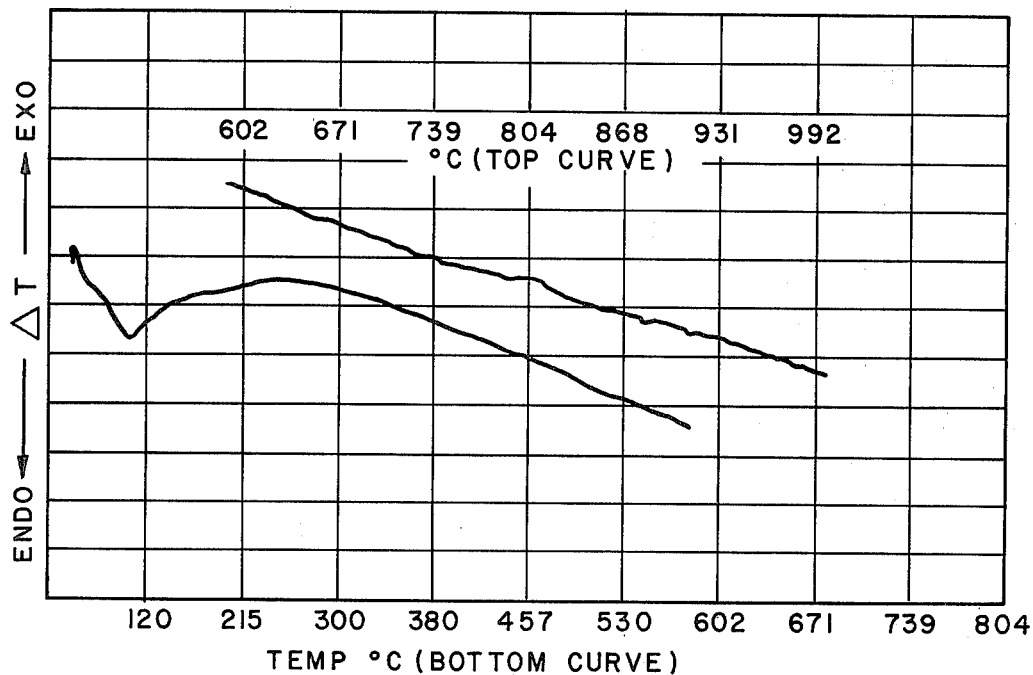
FIG. 3 is a Differential Thermal Analysis thermogram for aluminum hydroxide gel dried from ethanol.

The DTA pattern for the gel dried from water, FIG. 2, shows a large endotherm at 125° with a shoulder at 215°. The gel dried from ethanol, FIG. 3, gives a DTA pattern with a major endotherm at 120° with a slight shoulder at about 193°.

The difference in thermal behavior of the gel prepared by drying from ethanol is shown more clearly in the TGA and DTGA curves shown in FIGS. 4 and 5. From the TGA curves it appears that both gels have approximately the same water content of about 52%. The DTG curve for the gel dried from water shows water loss at about 94° and a second loss at about 207°. The rate of loss of water at 94° was 0.31 mg/min and 0.16 mg/min at 207°. The gel dried from ethanol lost water at 100° at the rate of 0.26 mg/min and at 207° at the rate of 0.17 mg/min.

The lower rate of loss of low temperature water in the gel dried from ethanol suggests that the water is less mobile in the gel and indicates that the arrangement of water in the dried gel prepared by the process of this invention is different than gels dried from water in the conventional manner.

The infrared spectrum for the gel prepared by drying from water, FIG. 6, has a very broad absorption band in the OH-stretching region 3700 to 3000 cm$^{-1}$ without any specific peaks of shoulders. The gel dried from ethanol, FIG. 7, also has a broad absorption band in the 3700 to 3000 cm$^{-1}$ region but also shows a very definite band at about 3280 cm$^{-1}$; indicating the presence of water molecules or hydrogen bonds having a unique environment. This band is associated with the water organization in the dried gel which promotes retention of high acid reactivity.

The aqueous aluminum hydroxide gel used in this invention can be prepared by any of the well-known methods, e.g., by the method described in the Journal of Pharmaceutical Sciences, 59, 517 (1970), wherein a soluble aluminum salt, such as aluminum chloride, aluminum sulfate and the like is added to a basic aqueous solution, such as an alkali metal carbonate and/or bicarbonate solution or an ammonium hydroxide solution. Alternately, the aluminum hydroxide gel may be prepared by the hydrolysis of an aluminum alkoxide such as aluminum isopropoxide as described in J. Pharm. Pharmacol. 13, 95T (1961) or U.S. Pat. No. 2,783,179, issued Feb. 26, 1969. As presently contemplated, the instant invention can be used with any liquid aluminum hydroxide gel regardless of the method used to prepare it.

In the process of this invention, the aqueous media of the liquid aluminum hydroxide gel is then replaced with a non-aqueous solvent such as indicated above. This can be done by any convenient method, e.g., by displacement by mixing with one or more portions of a water miscible non-aqueous solvent and decanting or filtering, or by extracting the water with a water miscible non-aqueous solvent and separating by standard techniques. The particular method used is not critical so long as it results in the replacement of the water in the liquid aluminum hydroxide gel with the water miscible non-aqueous solvent. It will be noted that the amount of non-aqueous solvent required in the process of this invention will depend on the method used to replace the water in the liquid aluminum hydroxide gel and the degree of miscibility of water in the non-aqueous solvent.

After replacement of the aqueous media in the gel with the non-aqueous solvent, the product is dried by standard techniques. Contemplated modes of drying include drying under vacuum at 25° C or at elevated temperatures, spray drying, forced air drying, drum drying and the like. The particular method used is not critical in the process of the instant invention in view of the heat stability of the final product.

In the preferred practice of this invention, an aqueous solution containing about 0.5 to 1.0 moles of aluminum chloride hexahydrate at a concentration of about 8.0 to 16.0% by weight is at room temperature added to an aqueous solution containing about 0.4 to 1.0 moles of sodium or potassium carbonate, preferably sodium carbonate at a concentration of about 1.0 to 5.0% by weight and 1.0 to 2.5 moles of sodium or potassium bicarbonate, preferably sodium bicarbonate, at a concentration of about 2 to 6% by weight. In place of the sodium or potassium carbonate or bicarbonate a quantity of ammonium carbonate sufficient to supply 0.5 to 1.5 moles of carbon dioxide when mixed with water can be used. The quantities and concentration of reactants are controlled so that the aluminum hydroxide gel is formed at pH of about 6.0 to 8.0. The product obtained is filtered and washed with de-ionized water until the concentration of chloride ion falls to less than 0.1%. The aqueous media is then replaced by adding a volume of one of the preferred non-aqueous solvents equal to the volume of the liquid aluminum hydroxide gel to the aqueous mixture and thoroughly mixing. The solvent and water are removed by decantation or vacuum filtration being careful to maintain the aluminum hydroxide gel as a moist cake. A second portion of the non-aqueous solvent is added and the moist cake is thoroughly redispersed by mixing. The vehicle is removed as before and the moist cake is treated with a third portion of the non-aqueous solvent. The aluminum hydroxide gel is dried from the non-aqueous solvent at room temperature under vacuum or in a forced air oven at temperatures up to 180° F.

The structure of these aluminum hydroxide gels is unknown. The commonly used designation $Al_2O_3$ or $Al(OH)_3$ does not accurately represent the composition of these materials as it is known that such materials can contain carbonate. This invention is based upon the inhibition of the development of ordering in the dried aluminum hydroxide gel and is accomplished by drying from solvents other than water. Antacid tablets prepared from the dried aluminum hydroxide gel of this invention exhibit the same in vitro reactivity as the liquid gel and the clinical effectiveness of these antacid tablets would be equivalent to the liquid dosage form. This results in an antacid dosage form having the effectiveness of liquid aluminum hydroxide and the convenience of a fully reactive dry dosage form.

EXAMPLE 1

In a 5 liter beaker, an 11.4% aqueous solution containing 0.755 moles of aluminum chloride hexahydrate is added to an aqueous solution containing 2.8% sodium carbonate (0.57 moles) and 4.5% sodium bicarbonate (1.336 moles). The mixture is stirred for a few minutes at room temperature; and the aluminum hydroxide gel formed is washed several times with de-ionized water to remove the residual chlorine.

The gel is then treated three times with a volume of ethanol equal to the volume of aluminum hydroxide gel (about 500 ml) by thoroughly dispersing the gel in the alcohol and filtering through a Buckner funnel using #1 filter paper being careful to maintain the aluminum hydroxide as a moist cake. The final product is dried at room temperature under vacuum.

Table I below shows the Rossett Rice time, lag time and acid consuming capacity on aging of the above dried aluminum hydroxide gel and similarly prepared gels dried from water and various other solvents. The Rossett Rice time and acid consuming capacity are described previously and the lag time is the length of time required for the pH to reach 3.0 after the addition of the hydrochloric acid commences in the Rossett Rice time determination.

40° (tests 11, 12, 13, 15, 16, 18 and 19) in comparison to the complete loss of Rossett Rice activity noted for the control (test 8).

The replacement of the aqueous vehicle with benzene or a mixture of 25% ethanol, (USP)/75% benzene does not improve the reactivity of the dried gels (tests 20 to 25).

The process of this invention is suitable for producing material which meets the U.S. Pharmacopeia (U.S.P.)

Table I

| Dried Form | Aging Conditions | %Al$_2$O$_3$ | Rossett Rice Time | Lag Time | Acid Consuming Capacity |
|---|---|---|---|---|---|
| 1) Liquid (not dried) | initial | 3.16 | 32 | 0 | 650 |
| 2) Water | initial | 34.2 | 26 | 0 | 650 |
| 3) Water | 10 days 40° | — | 23 | 1 | 650 |
| 4) Water | 2 months 40° | 38.6 | 10 | 3 | 640 |
| 5) Liquid (not dried) | initial | 3.47 | 26 | 0 | 625 |
| 6) Water | initial | 34.7 | 24 | 1 | 635 |
| 7) Water | 5 months 25° | — | 10 | 2 | — |
| 8) Water | 6 months 40° | 35.2 | 0 | — | 600 |
| 9) Commerical product | 1 year 25° | 50.8 | 0 | — | 570 |
| 10) Ethanol | initial | 36.2 | 30 | ½ | 650 |
| 11) | 10 days 40° | — | 30 | 1 | 650 |
| 12) | 2 months 40° | 43.5 | 16 | 5 | 650 |
| 13) | 6 months 40° | 35.2 | 19 | 4 | 650 |
| 14) Ethanol/benzene (3/1) | 2 months 25° | 44.2 | 26 | 4 | — |
| 15) | 5½ months 25° | — | 21 | 2 | — |
| 16) | 5¼ months 40° | 44.7 | 22 | 3½ | 635 |
| 17) Ethanol/benzene (1/1) | 2 months 25° | 33.3 | 28 | 3 | — |
| 18) | 5½ months 25° | — | 30 | 1 | — |
| 19) | 5½ months | 38.5 | 22 | 3 | 635 |
| 20) Ethanol/benzene (1/3) | 5 months 25° | 37.8 | 22 | 3 | — |
| 21) | 5 months 40° | 44.1 | 10 | 7¼ | 580 |
| 22) Liquid (not dried) | initial | 2.84 | 28 | 0 | 650 |
| 23) Water | initial | 26.8 | 26 | 0 | 650 |
| 24) Benzene | initial | 35.7 | 23 | ½ | 650 |
| 25) Benzene | 2 months 40° | 37.4 | 0 | — | 650 |

The temperatures shown in this table are in °C.

Dried aluminum hydroxide gels normally have a lowered acid reactivity compared to the original gel. This is seen in Table I by comparing the Rossett Rice time for liquid gels to the Rossett Rice time for these gels dried from their aqueous solvent (tests 2, 6 and 23). These dried gels are not stable as their acid reactivity measured by Rossett Rice Time and acid consuming capacity decreases when aged at 25 or 40° C (tests 3, 4, 7 and 8). A commercial dried aluminum hydroxide gel, test 9, had no Rossett Rice activity after 1 year at 25°.

Dried aluminum hydroxide gels dried from ethanol, absolute ethanol, and mixtures of ethanol and benzene containing 50 or 75% ethanol, retain the high acid reactivity of the original liquid gel, (tests 10, 14 and 17); and little or no change in acid consuming capacity was noted after 6 months at 40° in comparison to a 10% loss for gels dried from aqueous solvents. The high rate of reactivity retained by the gels dried from the non-aqueous solvents is shown by their relatively high Rossett Rice times after aging for 10 days to 6 months at 25° and specification for dried aluminum hydroxide gel, which specifications require dried aluminum hydroxide gel to contain no less than 50% of aluminum oxide (Al$_2$O$_3$). (See U.S. Pharmacopeia XVIII, page 27). It is submitted that material made by the process of this invention is more reactive and stable than heretofore produced material, with material produced being a free flowing powder that is not anhydrous.

The process of this invention takes fully hydrolyzed, amorphous aluminum hydroxide gel and replaces the water prior to drying. The data of Table I hereinabove utilized drying of gels under vacuum at room temperature. The following data (in Table II) shows that drying of the gel in a forced air oven yields material having a Al$_2$O$_3$ content greater than 50% (as is required to meet U.S.P. specifications) with high Rossett Rice time. This is in contrast with a great loss in reactivity that was found to occur when another portion of the gel was dried from its aqueous mother liquor.

Table II

Reactivity and Al$_2$O$_3$ Content of Aluminum Hydroxide

| Gel | Dried from | Time and Oven Temp. | Al$_2$O$_3$ | Rossett-Rice Time (for sample equivalent to 300 mg. Al$_2$O$_3$) | Lag Time |
|---|---|---|---|---|---|
| 2-42 | liquid (not dried) | — | 2.7% | 30½ | 0 |
| 2-42 | H$_2$O | vacuum dessicator at RT | 41.8% | 26 | 1 |
| 2-42 | H$_2$O | 5¾hr. at 122° F | 42.8% | — | — |
| 2-42 | H$_2$O | 6 hr. at 122° F | 44.1% | — | — |
| 2-42 | H$_2$O | 8¼ hr. at 122° F followed by 4 hrs. at 150° F | 45.8% | | |
| 2-42 | H$_2$O | 8¾ hrs. at 122° F | 47.3% | 23 | 3 |

Table II-continued

| | | | | Rossett-Rice Time | |
| | | | | (for sample equivalent | |
| Gel | Dried from | Time and Oven Temp. | $Al_2O_3$ | to 300 mg. $Al_2O_3$) | Lag Time |
|---|---|---|---|---|---|
| 2-42 | $H_2O$ | followed by 4 hrs. at 150° F followed by 3 hrs. at 170° F. 8¾ hrs. at 122° F followed by 4 hrs. at 150° F followed by 17 hrs. at 170° F | 48.6% | 22 | 4 |
| 2-42 | ethanol, USP | vacuum desiccator at RT | 40.3% | 28 | 1½ |
| 2-42 | ethanol, USP | 3½ hrs at 140° F | 49.2% | 26 | 1 |
| 2-42 | ethanol, USP | 6 hrs. at 140° F | 52.2% | 26 | 1 |
| 2-42 | ethanol, USP | 6 hrs. at 140° F followed by 14 hrs. at 180° F | 56.8% | 23 | 1½ |

Gel 2-42 was prepared by adding a solution of aluminum chloride to a solution of sodium carbonate and sodium bicarbonate.

It is to be appreciated that other drying means (for example, spray drying) could be utilized to effect the same results, i.e., sufficient effective drying to obtain an $Al_2O_3$ content greater than 50% to meet the U.S.P. specifications.

With respect to Table II, a gel (2–42) was divided in half. One portion was dried from alcohol by the method of this invention. As can be seen, the $Al_2O_3$ content increased with heating time. The alcohol washed material dried more readily and easily reached 50% $Al_2O_3$. The high Rossett Rice time was retained by the alcohol dried sample while the water dried sample lost reactivity upon drying.

The data in Table III below, demonstrates the improved reactivity of the alcohol dried material upon aging at 25° and 40° C in comparison to a portion of the same gel dried from water. Table III is as follows:

Table III

Stability of Alcohol-dried, Dried Aluminum Hydroxide Gel, USP

| Gel | Dried from $H_2O$ | Storage Temp | Storage Time | $Al_2O_3$ | Rossett-Rice Time (For Sample Equivalent To 300 mg $Al_2O_3$) | Lag Time |
|---|---|---|---|---|---|---|
| 2-69 | $H_2O$ | 40° | 1 mo | 50.3% | 21 | 4 |
| 2-69 | $H_2O$ | 40° | 32 mo | 50.3% | 7 | 7 |
| 2-69 | $H_2O$ | 25° | 2 mo | 50.0% | 20 | 4 |
| 2-69 | ethanol, USP | Initial (dried 4 hrs 120° F followed by 15 hrs 140° F) | — | 50.0% | 29 | 2 |
| 2-69 | ethanol, USP | 40° | 1 mo | 52.2% | 25 | 3 |
| 2-69 | ethanol, USP | 40° | 5½ mo | 52.2% | 24 | 4 |
| 2-69 | ethanol, USP | 40° | 32 mo | 52.2% | 20 | 5 |
| 2-69 | ethanol, USP | 25° | 36 mo | 50.0% | 23 | 4 |
| commerical product | $H_2O$ | 25° | 1 yr | 50.8% | 0 | — |

The alcohol dried gel (2–69) described in Table III passes all of the U.S.P. tests for dried aluminum hydroxide gel. The U.S.P. tests include: description, solubility, identification, reaction, acid consuming capacity, chloride, sulfate, arsenic, heavy metals, and assay. As is well known, a closed container is normally used to store the dried aluminum hydroxide gels. For example, the storage of dried aluminum hydroxide gels, as set forth in U.S. Pharmacopeia XVIII, page 27, specifies a tight container. The definition and standards for tight and well-closed containers are specifically set forth in U.S. Pharmacopeia (see U.S. Pharmacopeia XIX, pages 7-8 and pages 647-648).

Similar stable dried aluminum hydroxide gels are prepared when the sodium carbonate and sodium bicarbonate are replaced with equivalent amounts of potassium carbonate and potassium bicarbonate or ammonium carbonate, and when the water miscible non-aqueous solvent used is methanol or acetone.

Thus, the process of this invention is shown to yield a dried aluminum hydroxide gel that meets U.S.P. specifications.

What is claimed is:

1. A process for drying an aqueous aluminum hydroxide gel to form a stable dried aluminum hydroxide gel meeting the United States Pharmacopeia, Eighteenth Revision specification, said process comprising: replacing the aqueous liquid in the aluminum hydroxide gel with a water miscible, non-aqueous solvent, said non-aqueous solvent being selected from a group consisting of lower alkanols having 1 to 5 carbon atoms, mixtures of lower alkanols having 1 to 5 carbon atoms and no more than 50% of benzene and toluene mixed therewith, and ketones having 2 to 4 carbon atoms; and drying the gel of aluminum hydroxide removing the non-aqueous solvent and producing a stable, acid-reactant dried amorphous powder comprising not less than 50% and not more than about 56.8% of aluminum oxide.

2. A process as set forth in claim 1 in which the non-aqueous solvent is ethanol admixed with between 0% and 50% benzene.

3. A process as set forth in claim 1 in which the aqueous aluminum hydroxide gel is prepared by adding an aqueous solution of 0.5 to 1.0 moles of aluminum chloride to a solution containing 0.4 to 1.0 moles of sodium carbonate and 1.0 to 2.5 moles of sodium bicarbonate to precipitate the aluminum hydroxide gel within a pH range of 6.0 to 8.0.

4. A process as set forth in claim 3 in which the aqueous aluminum hydroxide gel is precipitated at a pH of 6.5 by adding 11.4% aqueous solution containing 0.755 moles of aluminum chloride hexahydrate to a solution containing 0.56 moles of sodium carbonate at a concentration of 2.8% by weight and 1.336 moles of sodium bicarbonate at a concentration of 4.5% by weight.

* * * * *